(12) United States Patent
Nakamura et al.

(10) Patent No.: US 9,099,350 B2
(45) Date of Patent: Aug. 4, 2015

(54) APPARATUS FOR INSPECTING INTEGRATED CIRCUIT

(75) Inventors: Tomonori Nakamura, Hamamatsu (JP); Nobuyuki Hirai, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 337 days.

(21) Appl. No.: 13/485,016

(22) Filed: May 31, 2012

(65) Prior Publication Data

US 2012/0307249 A1 Dec. 6, 2012

Related U.S. Application Data

(60) Provisional application No. 61/492,115, filed on Jun. 1, 2011.

(30) Foreign Application Priority Data

May 31, 2011 (JP) ................. 2011-121893

(51) Int. Cl.
*G01B 9/02* (2006.01)
*H01L 21/66* (2006.01)
(Continued)

(52) U.S. Cl.
CPC ............ *H01L 22/12* (2013.01); *G01N 21/55* (2013.01); *G01N 21/88* (2013.01)

(58) Field of Classification Search
CPC ......... H01L 22/12; G01N 21/55; G01N 21/88
USPC ............................ 356/237.1, 237.5, 450–521
See application file for complete search history.

(56) References Cited

U.S. PATENT DOCUMENTS

| 4,856,014 A | 8/1989 | Figueroa et al. |
| 5,465,043 A | 11/1995 | Sakai |

(Continued)

FOREIGN PATENT DOCUMENTS

| JP | 2000155099 A | 6/2000 |
| JP | 2007064975 A | 3/2007 |

OTHER PUBLICATIONS

Mark Davidson, Kalman Kaufman, Isaac Mazor, Felix Cohen, "An application of interference microscopy to integrated circuit inspection and metrology," Mar. 2, 1987, SPIE vol. 775 Integrated Circuit Metrology, Inspection, and Process Control, p. 233-247.*

(Continued)

*Primary Examiner* — Michael A Lyons
*Assistant Examiner* — Violeta A Prieto
(74) *Attorney, Agent, or Firm* — Drinker Biddle & Reath LLP

(57) ABSTRACT

An apparatus for inspecting an integrated circuit is an apparatus for inspecting an integrated circuit having a semiconductor substrate and a circuit portion formed on a front face a side of the semiconductor substrate. The apparatus comprises a light generation unit for generating light L for irradiating the integrated circuit, a wavelength width adjustment unit, for adjusting the wavelength width of the light irradiating the integrated circuit, an irradiation position adjustment unit for adjusting the irradiation position of the light irradiating the integrated circuit, and a light detection unit for detecting the light from the integrated circuit when the light from the light generation unit irradiates the circuit portion through a rear face of the semiconductor substrate.

7 Claims, 7 Drawing Sheets

(51) Int. Cl.
*G01N 21/55* (2014.01)
*G01N 21/88* (2006.01)

(56) References Cited

U.S. PATENT DOCUMENTS

| | | | |
|---|---|---|---|
| 5,956,142 A * | 9/1999 | Muller et al. | 356/504 |
| 6,184,542 B1 * | 2/2001 | Alphonse | 257/94 |
| 6,376,329 B1 | 4/2002 | Sogard et al. | |
| 6,690,469 B1 | 2/2004 | Shibata et al. | |
| 7,092,095 B2 * | 8/2006 | Shibata et al. | 356/369 |
| 7,304,798 B2 * | 12/2007 | Izumi et al. | 359/577 |
| 7,450,245 B2 | 11/2008 | Woods et al. | |
| 7,570,366 B2 * | 8/2009 | LeBlanc | 356/497 |
| 7,616,312 B2 | 11/2009 | Kasapi et al. | |
| 7,659,981 B2 | 2/2010 | Lo et al. | |
| 7,733,100 B2 | 6/2010 | Kasapi | |
| 7,745,836 B2 * | 6/2010 | Song et al. | 257/82 |
| 7,755,768 B2 * | 7/2010 | Mansfield | 356/497 |
| 7,808,653 B2 * | 10/2010 | LeBlanc | 356/513 |
| 7,990,167 B2 | 8/2011 | Kasapi | |
| 8,270,058 B1 * | 9/2012 | Muenter et al. | 359/238 |
| 2004/0150821 A1 * | 8/2004 | Shibata et al. | 356/369 |
| 2005/0117165 A1 * | 6/2005 | Holbrook et al. | 356/504 |
| 2005/0264813 A1 * | 12/2005 | Giakos | 356/369 |
| 2007/0046301 A1 * | 3/2007 | Kasapi | 324/751 |
| 2007/0188768 A1 * | 8/2007 | Mansfield | 356/504 |
| 2007/0293052 A1 | 12/2007 | Le Roy et al. | |
| 2008/0198366 A1 * | 8/2008 | LeBlanc | 356/73 |
| 2009/0141264 A1 * | 6/2009 | Shibata et al. | 356/51 |
| 2009/0152528 A1 * | 6/2009 | Song et al. | 257/13 |
| 2009/0237654 A1 * | 9/2009 | LeBlanc | 356/239.7 |
| 2010/0039131 A1 | 2/2010 | Kasapi | |
| 2010/0103250 A1 * | 4/2010 | Ishihara | 348/61 |

OTHER PUBLICATIONS

Kazumasa Takada, Norio Takato, and Juichi Noda, "Characterization of silica-based waveguides with an interferometric optical time-domain reflectometry system using a 1.3-mum-wavelength superluminescent diode", Jul. 1, 1989, Optics Letters, vol. 14, No. 13.*

Mertin, W., "Two-dimensional field mapping of monolithic microwave integrated circuits using electrooptic sampling techniques," Optical and Quantum Electronics 28, 1996, pp. 801-817.

Zhu, Z.H. et al., "New measurement technique: cw electrooptic probing of electric fields," Appl. Phys. Lett. 49, pp. 432-434, 1996.

Search Report from counterpart WO Patent Application No. PCT/JP2012/063521 issued Jul. 17, 2012 in Japanese language (8 pages).

Office Action issued Feb. 5, 2015 in European Patent Application No. 12793492.5.

* cited by examiner

Fig.5
(a)
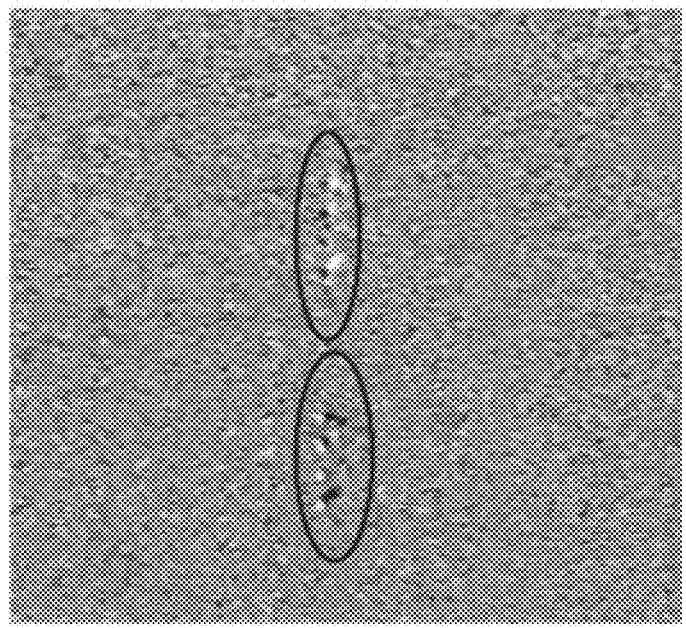
(b)
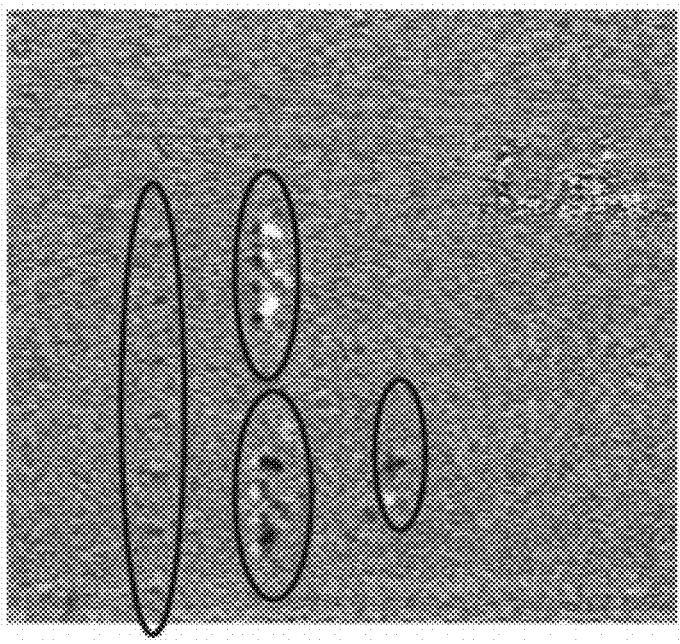

APPARATUS FOR INSPECTING INTEGRATED CIRCUIT

CROSS-REFERENCE TO RELATED APPLICATIONS

The present application claims the benefit of priority based on Japanese Patent Application No. 2011-121893 filed in Japan on May 31, 2011, and based on U.S. Provisional Patent Application No. 61/492,115 filed in the U.S. on Jun. 1, 2011. Each of these applications is incorporated by reference herein in its entirety.

BACKGROUND OF THE INVENTION

1. Field of the Invention

The present invention relates to an apparatus for inspecting an integrated circuit.

2. Related Background Art

As a technique concerning an apparatus for inspecting an integrated circuit, U.S. Patent Application Publication No. 2010/0039131 discloses a technique for irradiating an active region of a transistor formed in the integrated circuit with laser light and detecting the laser light modulated and reflected by the active region of the transistor, thereby analyzing a failure of the transistor. According to Patent Literature 1, the modulation of laser light depends on the transistor's response to a voltage applied to it, so that whether the transistor has a fault or not can be investigated by analyzing the amplitude, intensity, polarization rotation, or phase of the modulated laser light.

SUMMARY OF THE INVENTION

Since the technique disclosed in Patent Literature 1 irradiates the active region of the transistor with the laser light through the rear face of a semiconductor substrate, however, the laser light reflected by the rear face of the semiconductor substrate may interfere with the laser light modulated and reflected by the active region of the transistor. That is, interference information of the laser light reflected by the rear face may be superposed on signal information of the modulated laser light, so as to lower the S/N ratio. In addition, optical distances vary depending on expansions of the semiconductor substrate and changes in its refractive index caused by temperature variations, whereby the interference information is very hard to stabilize.

It is therefore an object of the present invention to provide an apparatus for inspecting an integrated circuit, which can improve the accuracy of inspecting the integrated circuit.

The apparatus for inspecting an integrated circuit in accordance with the present invention is an apparatus for inspecting an integrated circuit having a semiconductor substrate and a circuit portion formed on a front face side of the semiconductor substrate, the apparatus comprising a light generation unit for generating light for irradiating the integrated circuit, a wavelength width adjustment unit for adjusting a wavelength width of the light for irradiating the integrated circuit, an irradiation position adjustment unit for adjusting an irradiation position of the light for irradiating the integrated circuit, and a light detection unit for detecting light from the integrated circuit when the light from the light generation unit irradiates the circuit portion through a rear face of the semiconductor substrate.

In this apparatus, the wavelength width of the light irradiating the integrated circuit is adjusted by the wavelength width adjustment unit. This can increase the wavelength width (i.e., decrease the coherence length) according to the distance between the circuit portion and the rear face of the semiconductor substrate, for example, so as to inhibit the light reflected by the rear face of the semiconductor substrate (hereinafter referred to as "back-reflected light") from interfering with light from the circuit portion and its vicinity. That is, interference infoiination of the back-reflected light can be restrained from being superposed on signal information of light from the circuit portion and its vicinity and thus lowering the S/N ratio. Hence, this apparatus can improve the accuracy of inspecting the integrated circuit.

In the apparatus of the present invention, the light detection unit may detect an intensity of interfering light as the light from the integrated circuit. Since the back-reflected light is inhibited from interfering with the light from the circuit portion and its vicinity as mentioned above, the intensity of the interfering light detected by the light detection unit is mainly attributable to the light from the circuit portion and its vicinity. Therefore, the state of the circuit portion can be analyzed accurately according to the intensity of interfering light detected by the light detection unit.

In the apparatus of the present invention, the light generation unit may have a superluminescent diode, while the wavelength width adjustment unit may adjust the wavelength width by regulating a voltage applied to the superluminescent diode. Alternatively, the light generation unit may have a white light source, while the wavelength width adjustment unit may adjust the wavelength width by regulating a wavelength band of light to be transmitted therethrough in light from the white light source. These structures can appropriately adjust the wavelength width of the light irradiating the integrated circuit. Light with high luminance can be obtained in particular when the light generation unit has a superluminescent diode.

In the apparatus of the present invention, the irradiation position adjustment unit may adjust the irradiation position such that the light from the light generation unit irradiates the circuit portion through a depletion layer formed in the semiconductor substrate. In a MOS-type transistor unit, for example, this structure can irradiate the drain with light through the depletion layer, so as to detect the intensity of interfering light caused by light reflected by an interface of the drain on the depletion layer side (formed by a difference in material), light reflected by an interface of the depletion layer on the side opposite from the drain (formed by a difference in carrier density), and the like and thus can analyze the state of the circuit portion accurately.

In the apparatus of the present invention, the wavelength width adjustment unit may adjust the wavelength width according to a center wavelength of the light irradiating the integrated circuit, a refractive index of the semiconductor substrate, a thickness of the semiconductor substrate, and a depth of the depletion layer. When irradiating the circuit portion with light through the depletion layer, this structure can appropriately adjust the wavelength width of the light irradiating the integrated circuit in order to inhibit the back-reflected light from interfering with the light from the circuit portion and its vicinity and mainly detect the light from the circuit portion and its vicinity.

The present invention can improve the accuracy of inspecting the integrated circuit.

BRIEF DESCRIPTION OF THE DRAWINGS

[FIG. 5] is a set of pictures illustrating integrated circuit operation images as a comparative example and an example;

DESCRIPTION OF THE PREFERRED EMBODIMENTS

Figure 1:
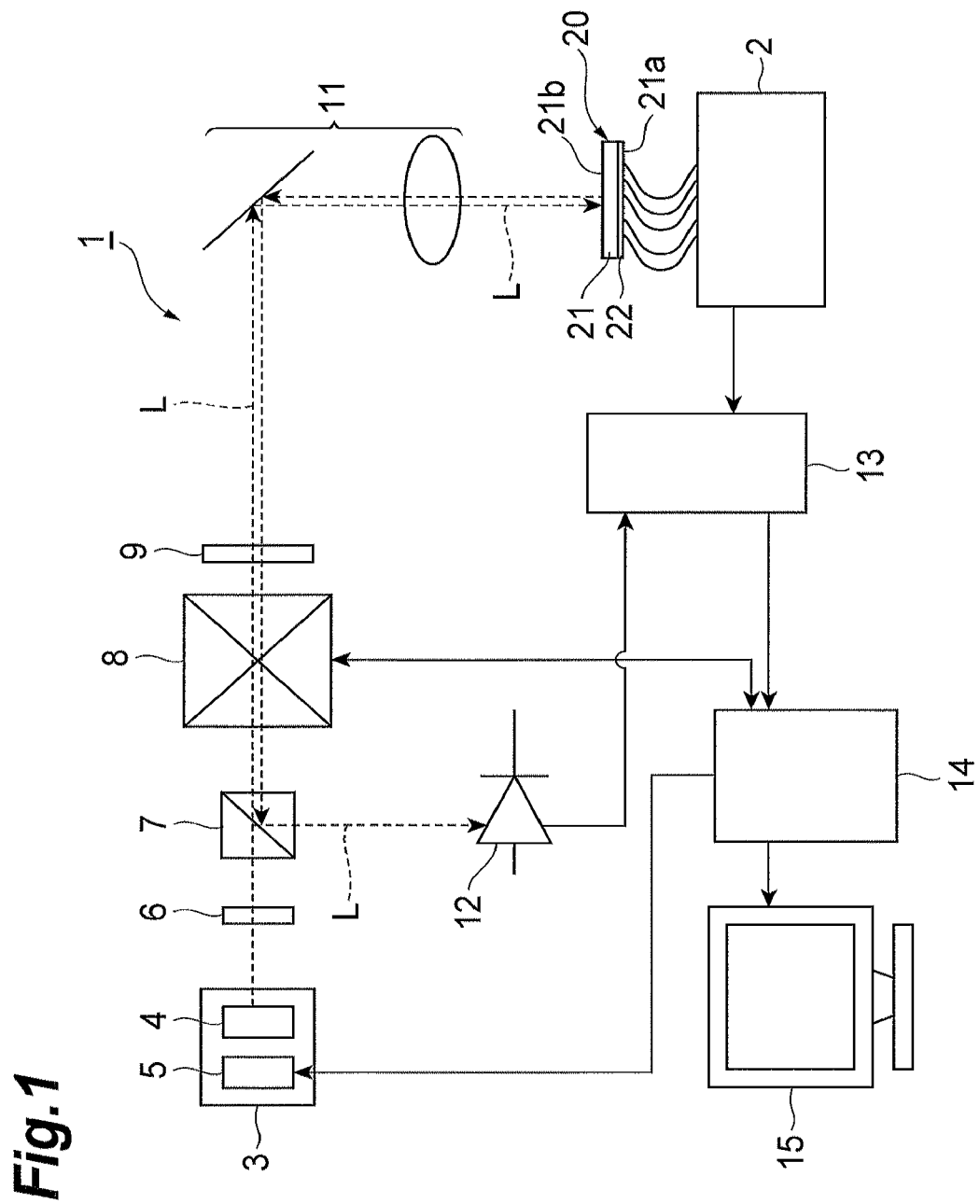
[FIG. 1] is a structural diagram of the apparatus for inspecting an integrated circuit in accordance with an embodiment of the present invention.

In the following, preferred embodiments of the present invention will be explained in detail with reference to the drawings. In the drawings, the same or equivalent parts will be referred to with the same signs while omitting their overlapping descriptions.

As illustrated in FIG. 1, an apparatus 1 for inspecting an integrated circuit is an apparatus for inspecting an integrated circuit 20, which is a device under test (DUT), so as to specify a location where an abnormality occurs, and so forth. The integrated circuit 20, an example of which is a C-MOS-IC, for example, having a silicon substrate (semiconductor substrate) 21 and a circuit portion 22 formed on a front face 21a side of the silicon substrate 21. A test signal (e.g., a pulse signal in a rectangular wave form) is fed into the integrated circuit 20, so as to drive the latter at the time of inspection.

The apparatus 1 is equipped with a light generation unit 3 for generating light L for irradiating the integrated circuit 20. The light generation unit 3 has a superluminescent diode (hereinafter referred to as "SLD") 4 and a voltage application unit 5 for applying a voltage to the SLD 4. The light L emitted from the SLD 4 when the voltage is applied thereto by the voltage application unit 5 is collimated into parallel light by a lens system and then exits from the light generation unit 3.

In the embodiments of this application incorporating SLD 4, the SLD is used rather than a laser source, for example, due to the comparatively superior performance which it provides. The SLD is a semiconductor light source exhibiting superluminescence. It has the high power and brightness of a laser diode, and the low coherence of a conventional light-emitting diode. Thus, the SLD is ideally suited for use in an integrated circuit inspecting apparatus, and an integrated circuit inspecting apparatus equipped with the SLD will be superior as compared to one equipped with a laser source, in terms of both structure and the performance which it yields. Among other things, the SLD will exhibit better performance than a laser source because, for example, the SLD will do a better job of suppressing interference because it has a shorter coherence length. These superior characteristics result in improved SNR (signal to noise ration) which, in turn, allows a better, higher-quality image to be obtained.

The light L exiting from the light generation unit 3 is converted by a polarizer 6 into linearly polarized light having a predetermined polarization direction. The light L transmitted through the polarizer 6 passes through a polarization beam splitter 7 and a scan optical system (irradiation position adjustment unit) 8 in sequence and then is converted by a quarter-wave plate 9 into circularly polarized light. The light L transmitted through the quarter-wave plate 9 forms an image at a predetermined position of the integrated circuit 20 through an image-forming optical system 11 including a mirror, a lens, and the like. At this time, the light L irradiates the circuit portion 22 through the rear face 21b of the silicon substrate 21. The scan optical system 8 two-dimensionally scans the integrated circuit 20 with the light L. That is, the scan optical system 8 adjusts the irradiation position of the light L irradiating the integrated circuit 20.

The light L reflected by the integrated circuit 20 passes through the image-forming optical system 11, so as to be converted by the quarter-wave plate 9 into linearly polarized light. The light L transmitted through the quarter-wave plate 9 passes through the scan optical system 8 but has a polarization direction perpendicular to the above-mentioned predetermined polarization direction, so as to be reflected by the polarization beam splitter 7, thereby being detected by a photosensor (light detection unit) 12. That is, when the light L from the light generation unit 3 irradiates the circuit portion 22 through the rear face 21b of the silicon substrate 21, the photosensor 12 detects the light L from the integrated circuit 20. Here, the photosensor 12 detects the intensity of interfering light as the light L from the integrated circuit 20.

An electric signal issued from the photosensor 12 in response to an input of the optical signal is amplified and then fed into a lock-in amplifier 13. According to the test signal fed from the tester 2 to the integrated circuit 20, the lock-in amplifier 13 extracts a signal corresponding to a specific period from the optical signal. Thus extracted signal is fed into a control unit 14 which controls individual parts of the apparatus 1 such as the scan optical system 8. The control unit 14 turns the input signal into an image in association with the position at which the integrated circuit 20 is irradiated with the light L. Thus produced integrated circuit operation image is shown on a display 15. A spectrum analyzer may be used in place of the lock-in amplifier 13.

The control unit 14 functions not only as an analysis unit, but also, together with the voltage application unit 5, as a wavelength width adjustment unit for adjusting the wavelength width of the light L irradiating the integrated circuit 20. That is, by controlling the voltage application unit 5 so as to regulate the voltage applied to the SLD 4, the control unit 14 adjusts the wavelength width of the light L irradiating the integrated circuit 20. The SLD 4 has such a characteristic as to emit the light L with narrower wavelength width as the voltage applied by the voltage application unit 5 is higher.

Figure 2:
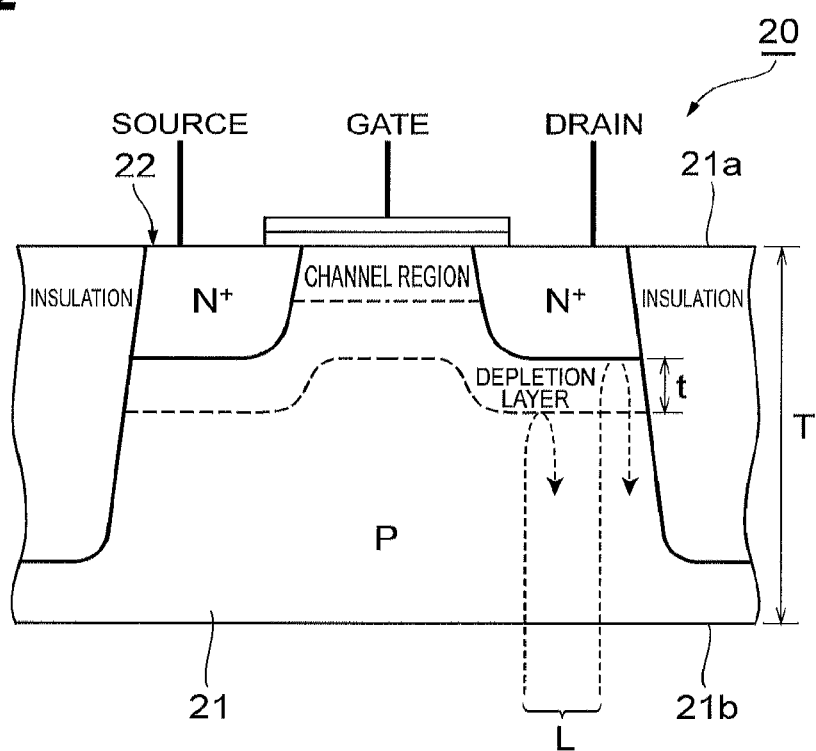
[FIG. 2] is a structural diagram of a part of an integrated circuit which is a device under test by the apparatus of FIG. 1.

The wavelength width of the light L adjusted by the control unit 14 will now be explained with reference to FIG. 2. FIG. 2 is a structural diagram of a MOS-type transistor unit which is a part of the integrated circuit 20. The position at which the integrated circuit 20 is irradiated with the light L is adjusted by the scan optical system 8 such that the circuit portion 22 (drain here) is irradiated with the light L through a depletion layer formed in the silicon substrate 21.

First, the coherence length l of light L is represented by the following expression:

$$l = \frac{2\ln 2}{n} \frac{\lambda^2}{d} = \frac{0.441}{n} \frac{\lambda^2}{d} \qquad [\text{Math. 1}]$$

where λ is the center wavelength (e.g., peak oscillation wavelength) of the light L, d is the wavelength width (e.g., spectral full width at half maximum) of the light L, and n is the refractive index of the medium through which the light L passes.

The intensity modulation of a signal effective in making the above-mentioned integrated circuit operation image is about several tens of ppm. That is, for reducing the noise relative to the signal so as to secure a sufficient S/N ratio, it is necessary for the coherence length l to be sufficiently small as compared with the optical path length difference between the component of light L reflected by the surface to be observed (i.e., the surface of the circuit portion 22 and its vicinity) and the component of light L reflected by the other surface (i.e., the rear face 21b of the silicon substrate 21). The intensity I of interfering light is represented by the following expression:

$$I = \left\{ \frac{\sin(\pi x/l)}{(\pi x/l)} \right\}^2 \quad [\text{Math. 2}]$$

where x is the distance from a position where the intensity I is maximized.

When |x|>1, assuming that the maximum value of intensity I is 1, the intensity I is approximately within the range of $$0 \leq I \leq 4/x^2\pi^2, \quad [\text{Math. 3}]$$

and, on average, $$I \approx 2/x^2\pi^2. \quad [\text{Math. 4}]$$

For improving the S/N ratio, it is necessary for the intensity I of interfering light between the component of light L reflected by the surface to be observed and the component of light L reflected by the other surface to be as low as possible. In order for the intensity I to be 0.001, for example, the distance x may be about 14. For suppressing the interference with the component of light L reflected by the rear face 21b of the silicon substrate 21, it is necessary for the optical path length by which the light L travels back and forth through the silicon substrate 21 to exceed the coherence length l.

That is, letting T be the thickness of the silicon substrate 21, and n be the refractive index of the silicon substrate 21 with respect to the light L, it is necessary to satisfy $$2Tn > 14\lambda^2/d, \text{ and} \quad [\text{Math. 5}]$$

$$d > 7\lambda^2/Tn. \quad [\text{Math. 6}]$$

The refractive index n of the silicon substrate 21 is about 3.5. The center wavelength (observation wavelength) of the light L is preferably as short as possible without being absorbed by the silicon substrate 21 and thus is typically 1.3 μm. In this case, the wavelength width d of the light L is represented by $$d > 3.38/T \text{ (unit: μm)}. \quad [\text{Math. 7}]$$

When the thickness T of the silicon substrate 21 is 100 μm, it is necessary for the wavelength width d of the light L to exceed 33.8 nm.

Thus making the light L have the broader wavelength width d and shorter coherence length l can inhibit the back-reflected light (the component of light L reflected by the rear face 21b of the silicon substrate 21) from interfering with the component of light L reflected by the surface of the circuit portion 22 and its vicinity.

On the other hand, the modulation of the reflected light of the light L is based on the change in reflectance on the surface of the circuit portion 22 and its vicinity, and this change is caused by the movement of the reflecting surface due to the expansion/shrinkage of the depletion layer near the circuit portion 22 and the light absorption by its inner carriers. That is, for preventing the change in reflectance from decreasing, a coherence length l which corresponds to 2 times the depth of the depletion layer (the distance between the interface of the drain on the depletion layer side and the interface of the depletion layer on the side opposite from the drain) multiplied by the refractive index n is necessary. This distance is in proportion to the square root of the voltage between regions in contact with each other and in reverse proportion to the carrier density. Letting t be the depth of the depletion layer accompanying a diffusion layer, the following expression holds:

$$2tn < 0.441\lambda^2/d. \quad [\text{Math. 8}]$$

Letting the refractive index n of the silicon substrate 21 be 3.5, and the center wavelength of the light L be 1.3 μm as mentioned above, approximately $$d < 0.106/t \text{ (unit: μm)}. \quad [\text{Math. 9}]$$

Hence, an appropriate wavelength width d of the light L is represented by $$3.38/T \leq d \leq 0.106/t \text{ (unit: μm)}. \quad [\text{Math. 10}]$$

When observing also the voltage of a deep diffusion layer (well structure) or the like, assuming that the depth t of the depletion layer and the thickness T of the silicon substrate 21 are 1 μm and 100 respectively, the appropriate wavelength width d of the light L is represented by $$33.8 < d < 106 \text{ (unit: nm)}. \quad [\text{Math. 11}]$$

As in the foregoing, the control unit 14 determines the value of wavelength width d of the light L according to the center wavelength λ of the light L irradiating the integrated circuit 20, the refractive index n of the silicon substrate 21, the thickness T of the silicon substrate 21, and the depth t of the depletion layer. The control unit 14 controls the voltage application unit 5, so as to regulate the voltage applied to the SLD 4, thereby adjusting the wavelength width d such that it attains the determined value.

The making of the above-mentioned integrated circuit operation image will now be explained. Here, the making of the integrated circuit operation image is based on the LVI (Laser Voltage Imaging) method (see, for example, Patent Literature 1).

Figure 3:
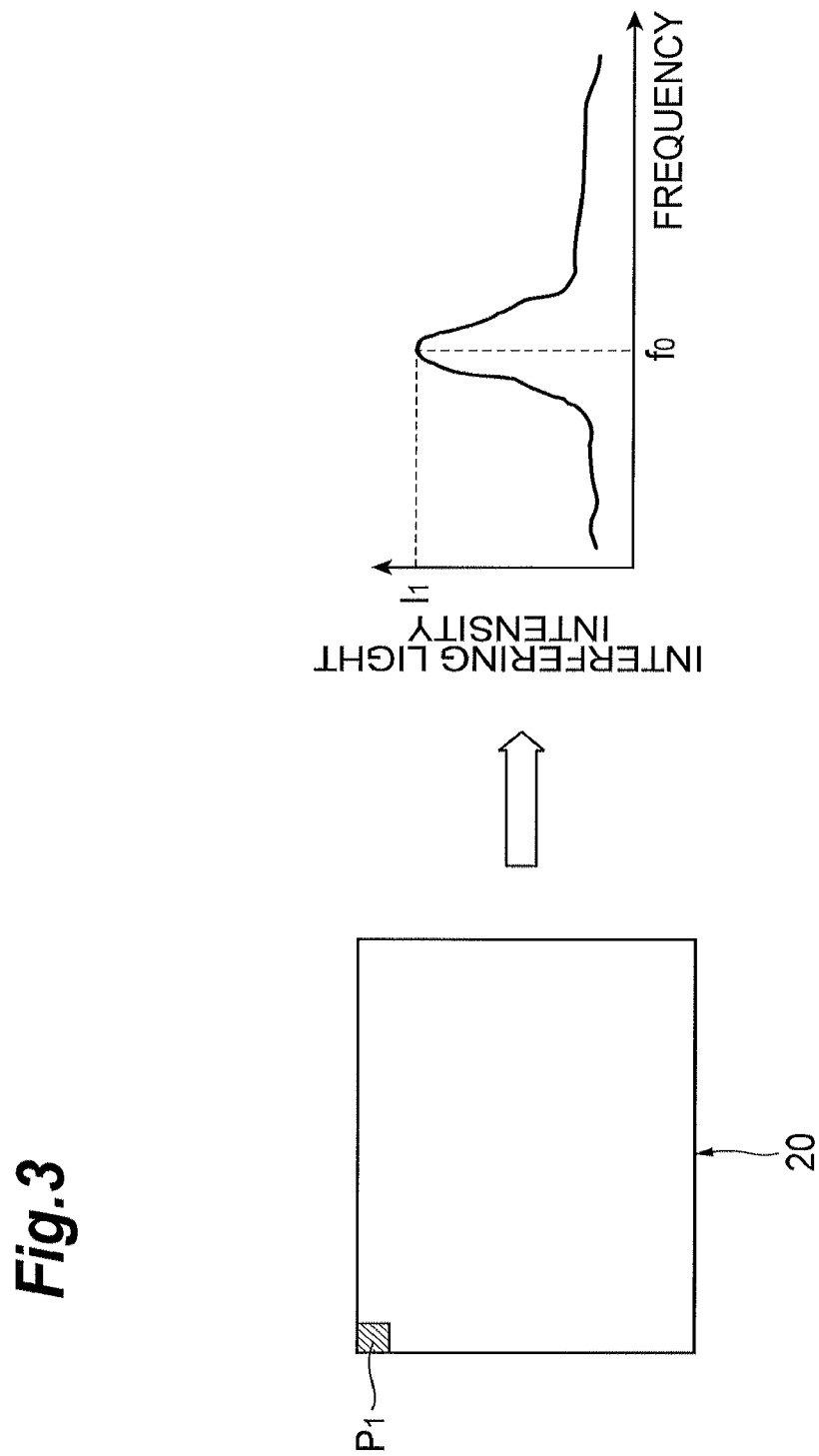
[FIG. 3] is an explanatory view of making an integrated circuit operation image by using the apparatus of FIG. 1.

First, the tester 2 feeds the test signal to the integrated circuit 20, so as to drive the latter. In this state, as illustrated in FIG. 3, the position where the integrated circuit 20 is irradiated with the light L is placed at a position $P_1$ by the scan optical system 8, and the intensity of interfering light is detected by the photosensor 12. Then, the lock-in amplifier 13 analyzes the intensity signal of the interfering light in synchronization with the test signal, so as to detect the intensity $I_1$ of the interfering light at a specific frequency $f_0$.

Figure 4:
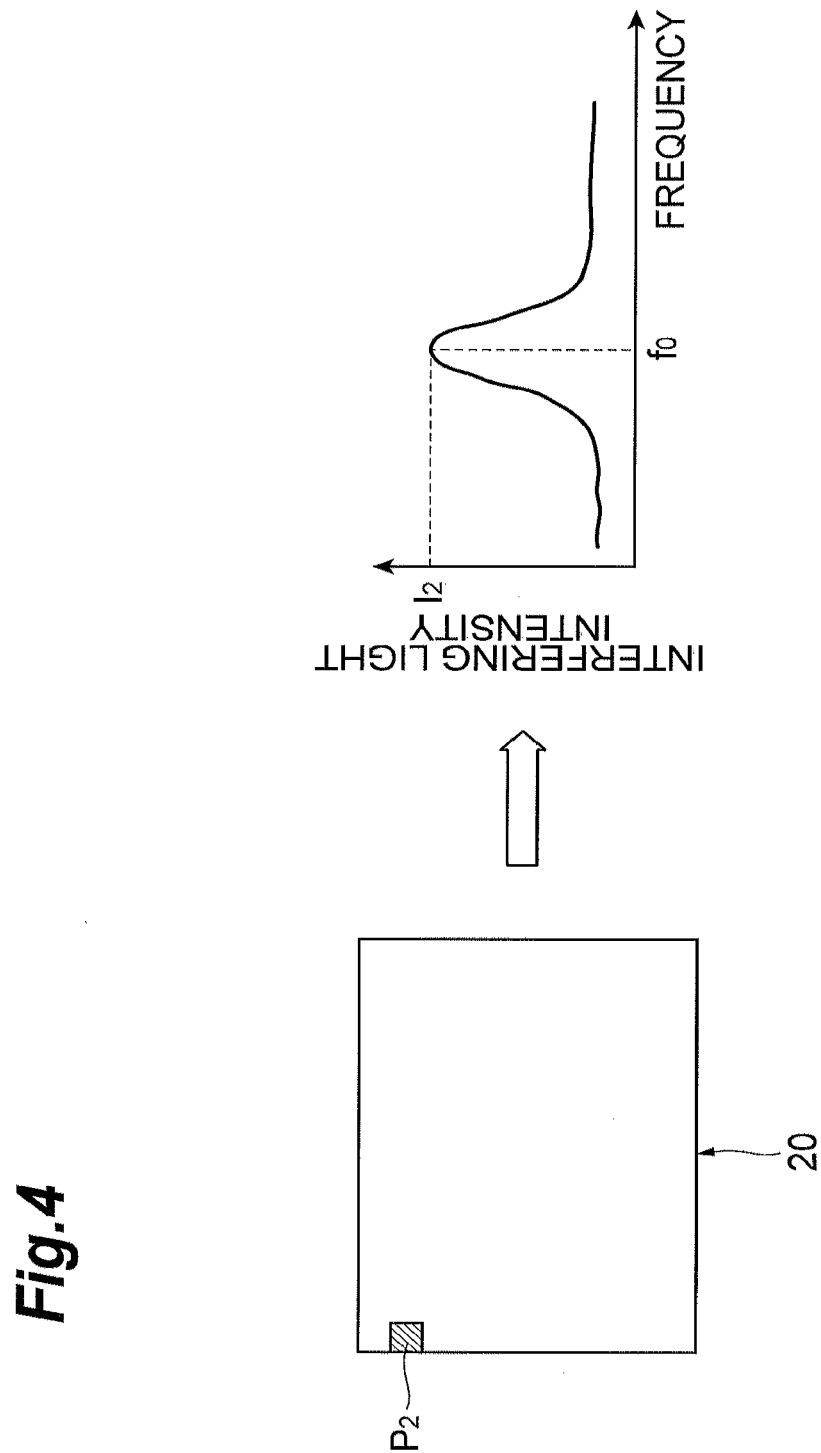
[FIG. 4] is an explanatory view of making an integrated circuit operation image by using the apparatus of FIG. 1.

Subsequently, as illustrated in FIG. 4, the position where the integrated circuit 20 is irradiated with the light L is placed at a position $P_2$ by the scan optical system 8, and the intensity of interfering light is detected by the photosensor 12. Then, the lock-in amplifier 13 analyzes the intensity signal of the interfering light in synchronization with the test signal, so as to detect the intensity $I_2$ of the interfering light at the specific frequency $f_0$.

Thus, the integrated circuit 20 is two-dimensionally scanned with the irradiation position of the light L, so as to detect the intensity $I_2$ at the specific frequency $f_0$ in the entire integrated circuit 20. Then, the control unit 14 associates the intensity of interfering light with the irradiation position of the light L, so that an interfering light intensity image at the specific frequency $f_0$ is made as an integrated circuit operation image, which is shown on the display 15.

Whether the integrated circuit 20 is driven or not alters the range where carriers exist in the circuit portion 22, thereby modifying the depth of the depletion layer, its light absorptance, and the like. This changes the optical path length of the light L reflected by the interface of the depletion layer on the side opposite from the drain. Therefore, a change in intensity (intensity modulation) of the light L exists between the cases where the integrated circuit 20 is driven and not, whereas the intensity of the light L reflected by the interface does not change at a location where an abnormality occurs. Hence, detecting the intensity of the interfering light can specify the location where the abnormality occurs in the integrated circuit 20. The irradiation position of the light L may be placed at a specific location in the integrated circuit 20, so as to detect the intensity of the interfering light at this location, thereby inspecting the location.

In the apparatus 1, as explained in the foregoing, the wavelength width of the light L irradiating the integrated circuit 20 is adjusted by the control unit 14 and voltage application unit 5. This can increase the wavelength width (i.e., decrease the coherence length) according to the distance between the circuit portion 22 and the rear face 21b of the silicon substrate 21, so as to inhibit the back-reflected light from interfering with the light L from the circuit portion 22 and its vicinity. That is, interference information of the back-reflected light can be restrained from being superposed on signal information of the light L from the circuit portion 22 and its vicinity and thus lowering the S/N ratio. Hence, the apparatus 1 can improve the accuracy of inspecting the integrated circuit 20.

The light generation unit 3 has the SLD 4, while the control unit 14 controls the voltage application unit 5, so as to regulate the voltage applied to the SLD 4, thereby adjusting the wavelength width of the light L irradiating the integrated circuit 20. This can appropriately adjust the wavelength width of the light L irradiating the integrated circuit 20. Using the SLD 4 can yield the light L with high luminance in particular.

A wavelength-selective filter for adjusting the wavelength width of the light L may be arranged on an optical path of the light L emitted from the SLD 4. In this case, the control unit 14 functions, together with the wavelength-selective filter, as the wavelength width adjustment unit for adjusting the wavelength width of the light L irradiating the integrated circuit 20. That is, by switching among several kinds of wavelength-selective filters (e.g., any of bandpass filters, long-pass filters, and short-pass filters or their combinations), for example, the control unit 14 regulates the wavelength band of the light L to pass therethrough from the SLD 4, so as to adjust the wavelength width of the light L irradiating the integrated circuit 20. This can also appropriately adjust the wavelength width of the light L irradiating the integrated circuit 20.

Here, the control unit 14 determines the value of wavelength width of the light L irradiating the integrated circuit 20 according to the center wavelength of the light L, the refractive index of the silicon substrate 21, the thickness of the silicon substrate 21, and the depth of the depletion layer. This can appropriately adjust the wavelength width of the light L irradiating the integrated circuit 20 in order to inhibit the back-reflected light from interfering with the light L from the circuit portion 22 and its vicinity and mainly detect the light L from the circuit portion 22 and its vicinity.

The scan optical system 8 adjusts the irradiation position of the light L such that the light L from the light generation unit 3 irradiates the circuit portion 22 through the depletion layer formed in the silicon substrate 21. In a MOS-type transistor unit, for example, this structure can irradiate the drain with the light L through the depletion layer, so as to detect the intensity of interfering light caused by light reflected by an interface of the drain on the depletion layer side (formed by a difference in material), light reflected by an interface of the depletion layer on the side opposite from the drain (formed by a difference in carrier density), and the like and thus can analyze the state of the circuit portion 22 accurately. The width of a channel region between the source and drain has recently been becoming narrower than the wavelength of the light L as the integrated circuit 20 has been made finer, so that the light L is harder to be incident on this region, whereby the above-mentioned structure can be very effective. The circuit portion 22 may also be irradiated with the light L from the light generation unit 3 through a depletion layer directly under the channel region.

FIG. 5 is a set of pictures illustrating integrated circuit operation images as a comparative example and an example. As the comparative example, laser light having a center wavelength of 1300 nm, a wavelength width of 1 nm or less, and an output of 109 mW was emitted, so as to acquire an integrated circuit operation image by LVP, and driven parts were surrounded by ellipses (FIG. 5(a)). As the example, on the other hand, light having a center wavelength of 1310 nm, a wavelength width of 55 nm, and an output of 14 mW was emitted, so as to acquire an integrated circuit operation image by LVP, and driven parts (active parts) were surrounded by ellipses (FIG. 5(b)). The same integrated circuit was used as the device under test. As a result, when compared with the irradiation with the laser light having the center wavelength of 1300 nm, wavelength width of 1 nm or less, and output of 109 mW, the irradiation with the light having the center wavelength of 1310 nm, wavelength width of 55 nm, and output of 14 mW lowered the noise generated under the influence of the back-reflected light, so that the driven parts were seen even in regions where no driven parts were found when irradiated with the laser light.

Figure 6:
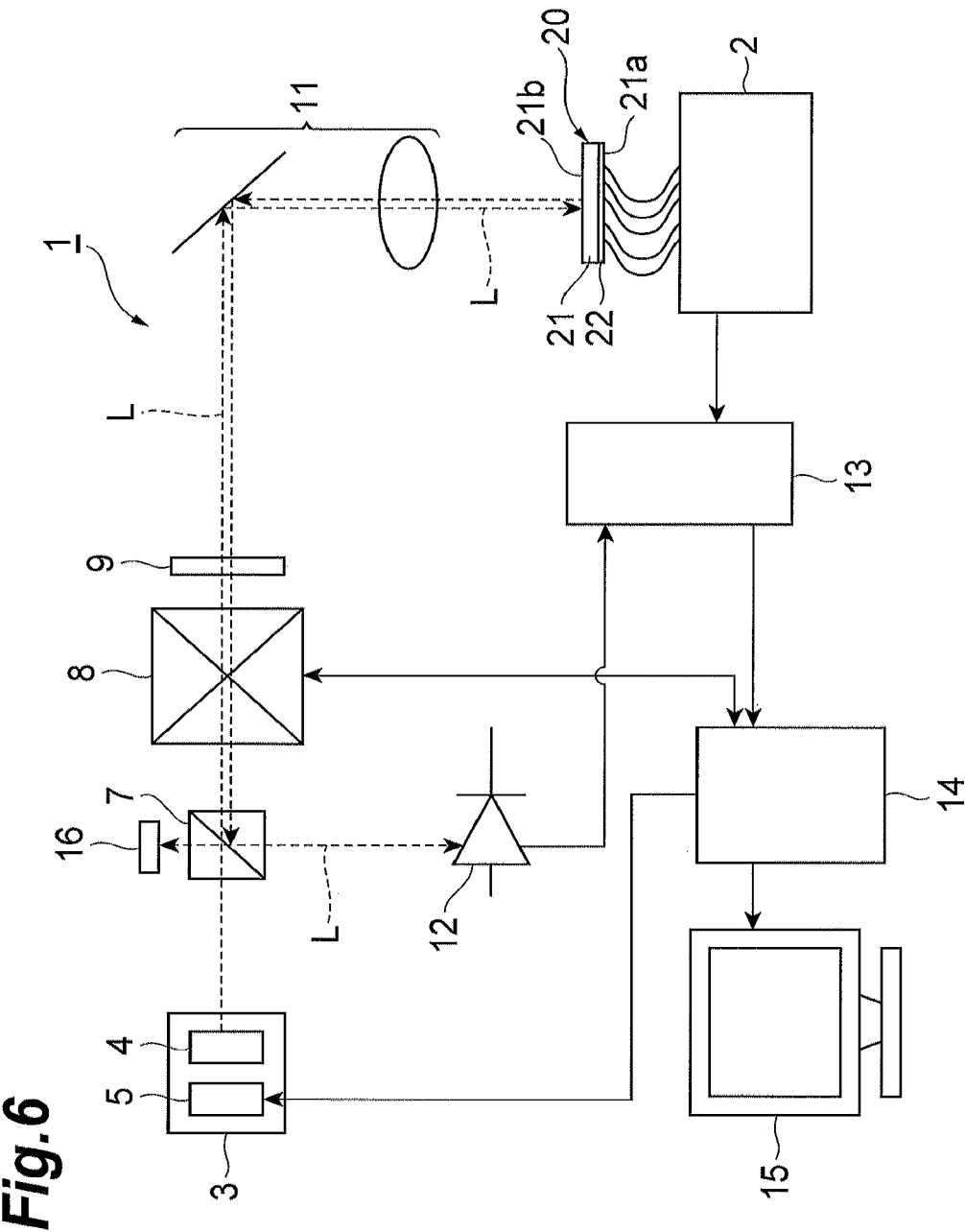
[FIG. 6] is a structural diagram of the apparatus for inspecting an integrated circuit in accordance with another embodiment of the present invention.

Though an embodiment of the present invention has been explained in the foregoing, the present invention is not limited thereto. For example, as illustrated in FIG. 6, it is not necessary for the polarizer 6 to be arranged between the SLD 4 and the polarization beam splitter 7. In this case, for preventing nonlinearly polarized components in the light L emitted from the SLD 4 from being directed to the photosensor 12 as scattered light, a light absorber 16 such as a black member which absorbs these components may be arranged on a side of the polarization beam splitter 7 opposite from the photosensor 12.

Figure 7:
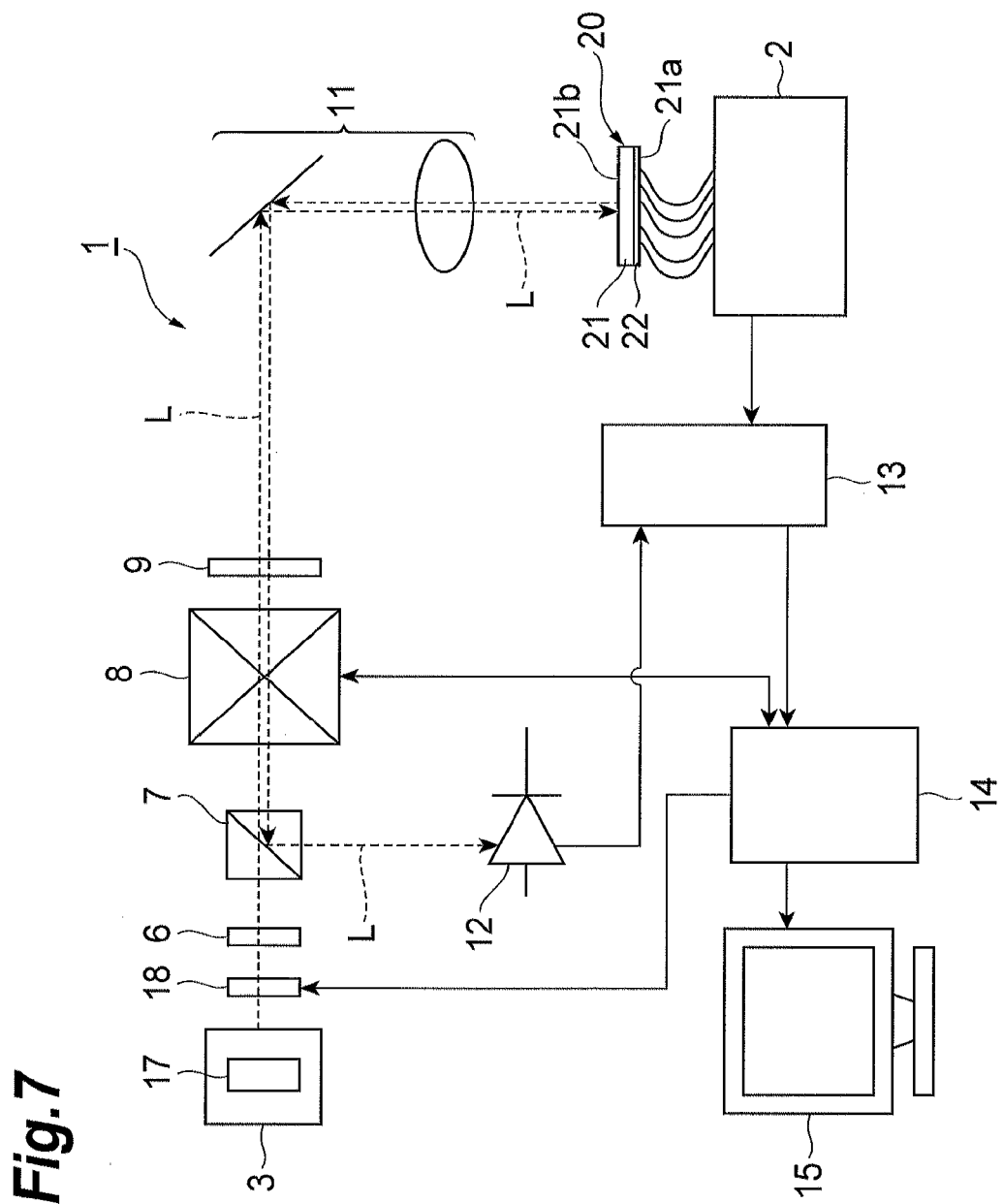
[FIG. 7] is a structural diagram of the apparatus for inspecting an integrated circuit in accordance with still another embodiment of the present invention.

As illustrated in FIG. 7, the light generation unit 3 may have a white light source 17 in place of the SLD 4. In this case, a wavelength-selective filter 18 for adjusting the wavelength width of the light L may be arranged on the optical path of the light L emitted from the white light source 17. Here, the control unit 14 functions, together with the wavelength-selective filter 18, as the wavelength width adjustment unit for adjusting the wavelength width of the light L irradiating the integrated circuit 20. That is, by switching among several kinds of wavelength-selective filters (e.g., any of bandpass filters, long-pass filters, and short-pass filters or their combinations), for example, the control unit 14 regulates the wavelength band of the light L to pass therethrough from the white light source 17, so as to adjust the wavelength width of the light L irradiating the integrated circuit 20. This can also appropriately adjust the wavelength width of the light L irradiating the integrated circuit 20.

What is claimed is:
1. An apparatus for inspecting an integrated circuit having a semiconductor substrate and a circuit portion formed on a front face side of the semiconductor substrate, the apparatus comprising:
a superluminescent diode configured to output light having a wavelength width;
a scan optical system configured to receive the outputted light and adjust an irradiation position of the outputted light and configured to receive reflected light that is reflected from the integrated circuit; and a photosensor configured to detect the reflected light.

2. The apparatus according to claim 1, wherein the photosensor detects an intensity of interfering light as the reflected light.

3. The apparatus according to claim 1, further comprising:
a wavelength width adjustment unit configured to adjust the wavelength width by regulating a voltage applied to the superluminescent diode.

4. The apparatus according to claim 1, wherein the scan optical system adjusts the irradiation position such that the outputted light irradiates the circuit portion through a depletion layer formed in the semiconductor substrate.

5. The apparatus according to claim 4, further comprising:
a wavelength width adjustment unit configured to adjust the wavelength width according to a center wavelength of the light irradiating the integrated circuit, a refractive index of the semiconductor substrate, a thickness of the semiconductor substrate, and a depth of the depletion layer.

6. The apparatus according to claim 1, wherein the wavelength width is more than 33.8 nm.

7. The apparatus according to claim 1, wherein the light having the wavelength width includes light having a wavelength of 1.3 μm.

* * * * *